(12) United States Patent
De Munck et al.

(10) Patent No.: US 9,725,401 B2
(45) Date of Patent: Aug. 8, 2017

(54) PROCESSES FOR THE PRODUCTION OF ESTERS

(75) Inventors: Nicolaas A. De Munck, Barendrecht (NL); Eddy T. A. Van Driessche, Eeklo (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 13/805,951

(22) PCT Filed: Jul. 19, 2011

(86) PCT No.: PCT/EP2011/062366
§ 371 (c)(1),
(2), (4) Date: Feb. 20, 2013

(87) PCT Pub. No.: WO2012/025308
PCT Pub. Date: Mar. 1, 2012

(65) Prior Publication Data
US 2014/0148612 A1 May 29, 2014

Related U.S. Application Data

(60) Provisional application No. 61/376,855, filed on Aug. 25, 2010.

(30) Foreign Application Priority Data

Oct. 13, 2010 (EP) .................................... 10187365

(51) Int. Cl.
| C07C 69/76 | (2006.01) |
| C07C 69/78 | (2006.01) |
| C07C 67/08 | (2006.01) |

(52) U.S. Cl.
CPC .............. C07C 69/78 (2013.01); C07C 67/08 (2013.01); *Y02P 20/582* (2015.11)

(58) Field of Classification Search
CPC .................................................... C07C 67/08
USPC .......................................... 560/103, 99, 204
See application file for complete search history.

(56) References Cited

U.S. PATENT DOCUMENTS

| 2,867,651 | A | * | 1/1959 | Wise ............................... 560/98 |
| 3,056,818 | A | | 10/1962 | Werber |
| 3,480,575 | A | | 11/1969 | Coats et al. |
| 5,324,853 | A | | 6/1994 | Jones et al. |
| 5,349,075 | A | | 9/1994 | van den Berg et al. |
| 6,235,924 | B1 | | 5/2001 | McConnell et al. |
| 7,629,413 | B2 | | 12/2009 | Godwin et al. |

FOREIGN PATENT DOCUMENTS

| WO | WO 2005/021482 | 3/2005 |
| WO | WO 2006/125670 | 11/2006 |
| WO | WO 2008/110305 | 9/2008 |
| WO | WO 2008/110306 | 9/2008 |
| WO | WO 2009/038900 | 3/2009 |
| WO | WO 2011/001244 | 1/2011 |
| WO | WO 2012/025308 | 3/2012 |

OTHER PUBLICATIONS

Cole, A.C. et al., *Novel Bronsted Acidic Ionic Liquids and Their Use as Dual Solvent-Catalysts*, Journal of the American Chemical Society, American Chemical Society, Washington, DC; US, vol. 124, May 7, 2002 pp. 5962-5963.
*Esterification*, Kirk-Othmer Encyclopedia of Chemical Technology, Fourth Edition, vol. 9, 1994, pp. 762-768.
Awaj, Firas et al., *Design Aspects of Used Lubricating Oil Re-Refining*, REFEREX, XP040425887, Elsevier B.V., First Edition, (Jan. 1, 2006), pp. 1-81.

* cited by examiner

*Primary Examiner* — Sudhakar Katakam
*Assistant Examiner* — Ana Z Muresan
(74) *Attorney, Agent, or Firm* — Darryl M. Tyus

(57) ABSTRACT

A process for production of $C_4$ to $C_{15}$ esters by the esterification of a carboxylic acid or anhydride with a $C_4$ to $C_{15}$ alcohol including forming a reaction mixture of the acid or anhydride and the $C_4$ to $C_{15}$ alcohol including a stoichiometric excess of the alcohol is provided.

20 Claims, 6 Drawing Sheets

PROCESSES FOR THE PRODUCTION OF ESTERS

CROSS REFERENCE TO RELATED APPLICATIONS

This application is a 371 National Stage Application of International Application No. PCT/EP2011/062366, filed Jul. 19, 2011, that claims the benefit of Application No. 61/376,855, filed Aug. 25, 2010, and EP 10187365.1, filed Oct. 13, 2010, the disclosures of which are incorporated by reference in their entireties.

FIELD OF THE INVENTION

Embodiments disclosed herein generally relate to improvements in or relating to esterification processes and in particular to esterification processes of acids and anhydrides with alcohols, particularly, for the production of esters of phthalic acid and anhydrides, adipic acid, trimellitic, cyclohexane carboxylic acids, and benzoic acid and $C_4$ to $C_{15}$ alcohols.

BACKGROUND OF THE INVENTION

Esters are most commonly prepared by the reaction of an acid and an alcohol accompanied by the elimination of water. Esters may also be formed by reaction of an alcohol with various other reactants including acid anhydrides, acid chlorides, amides, nitriles, aldehydes, and ketones. Mixtures of acids and/or alcohols may also be used as starting materials. The same may apply for the other reactants.

The reaction conditions under which esterification is effected may be varied considerably. The reaction proceeds very slowly at room temperature but quite rapidly at elevated temperatures when the mixture is at optimum reaction temperature heat is provided to promote the reaction at that temperature. Typically one of the reactants is used in stoichiometric excess in order to drive the reaction. The other reactant is then called the limiting reagent. About 99% of the limiting reagent may be converted to an ester within a few hours. The acid or anhydride is usually the limiting reagent and the alcohol is usually present in an excess.

Because the esterification of an alcohol and an organic acid or anhydride is a reversible reaction, the esterification reaction normally does not go to completion. However, conversions of over 99% may be achieved by removing at least one of the esterification products during the reaction and this removal is typically achieved by distillation. Typically water is removed. A variety of distillation techniques are known in the art to remove the produced water from the reaction zone. One method of water removal includes carrying out the reaction in a liquid medium which may form an azeotrope having a boiling point that is lower than that of either or each component of the reaction. If the reagents and the resulting ester have boiling points above 100° C. at atmospheric pressure, then the reaction temperature can be adjusted such that no liquid medium capable of forming an azeotrope with water is required. Additionally, an entrainer may be used to aid in the distillation of the water from the reaction mixture. Inert materials such as cyclohexane, hexane, benzene, toluene, or xylene may be used as an entrainer. In addition, the reactant having the lower boiling point may also be employed as the entrainer. In this case, the reactant used as the entrainer is typically charged into the reaction mixture in excess over the stoichiometric quantities required for the reaction. Esterification processes, including those employing water removal, may be conducted in a batch or continuous mode of operation. Various esterification processes are disclosed in Volume 9 of the Kirk-Othmer Encyclopaedia of Chemical Technology, Fourth Edition (1994), pp. 762-768.

A conventional batch esterification procedure includes charging all of the reactants into the reactor at the beginning of the reaction cycle. In catalytic esterification processes, the catalyst is typically added to the reaction mixture after the batch reaches a target temperature. The temperature of the reaction mixture rises until the boiling point of the reaction mixture is achieved, at which point the entrainer, and water by-product boil out of the reaction mixture. The reaction mixture may then be heated further and is vigorously stirred to promote the reaction at that temperature. Typically, the overhead vapours are condensed, the water separated from the entrainer, and the entrainer recycled to the reactor vessel. The reaction temperature, and therefore the rate of reaction, is limited by the boiling point of the reaction mixture. When the reactant with the lower boiling point (usually the alcohol) is also used as the entrainer, its concentration is gradually reduced as the reaction proceeds. Also the concentrations of the reactants decrease during the reaction, which negatively affects the reaction rate. Thus, the reaction temperature, and, therefore, the rate constant for the reaction, increases as the reaction proceeds, irrespective whether an entrainer is used or not, particularly if heat input is continued during the course of the reaction.

Conventional esterification processes may be accomplished in two reaction steps. The first reaction step generally occurs in the absence of an esterification catalyst, while the second reaction step may include the use of an esterification catalyst. In U.S. Pat. No. 5,349,075, a two step esterification process with a first uncatalyzed esterification reaction step conducted at a temperature of at least 200° C., i.e., conditions whereby the more volatile reactant is in the gaseous phase while the less volatile reactant is in the liquid phase, followed by a catalyzed second esterification reaction step at a temperature below 100° C. is proposed. The process employs a solid acid catalyst in the second reaction step. Other background references include U.S. Pat. No. 6,235,924.

In the commercial production of esters, conversions of greater than 99% are desired.

Most esterification processes are capable of converting about 99% of the limiting reagent, such as acids, anhydrides or polyols, to an ester within a few hours of reaction time; however, after about 90% of the limiting reagent is converted, the rate of reaction tends to slow down substantially. It may take half as long again to convert the remaining 4-5% of limiting reagent as it took to convert the initial 95% thereof.

The esterification reaction produces water and since the titanium or tin esterification catalysts that are typically used are water sensitive, it is necessary to minimize contact between the water produced in the reaction and the catalyst. Accordingly, it has been practice to distil off as much as possible of any water of reaction during the initial phases of the reaction prior to addition of the catalyst. However, this process requires a relatively long cycle time and also involves boiling off and recycle of reactants, particularly the alcohol. Generally, the alcohol is recycled by reflux which is typically subcooled and can therefore lower the temperature of the reaction mixture and further prolong the reaction cycle time, in particular when heat input capabilities are limited which is usually the case in an industrial setting.

Titanates are often used as esterification catalysts. The reaction is performed at elevated temperature with vigorous stirring so that thermal and mechanical energy is imparted to the reaction mixture. About 20% excess of alcohol is used to push the equilibrium of the reaction towards the formation of the ester and to act as a water entrainer. Water is formed during the reaction and is removed with boiling alcohol. The water/boiling alcohol mixture passes to a condenser and a separator where the water is separated from the alcohol which is recycled to the reactor and the water is removed. In order to maintain sufficient alcohol boil-up pressure in the reactor can be gradually reduced as the reaction progresses.

WO2008/110306 relates to the use of a particular temperature and pressure profile during a batch esterification process.

One problem associated with this esterification process is that the reaction mixture tends to foam so that the alcohol that is boiled off during the reaction carries with it some of the acid or anhydride, some of the catalyst, and can also carry some of the ester that has been produced. This reduces the yield of the reaction and also leads to product impurities. The problem is particularly acute with the esterification of monobasic acids such as benzoic acid in view of the larger amount of water that is formed. In the esterification reaction, excessive foaming can result in the reactor overhead becoming inoperative, refluxing of emulsions, and undesirable fluctuations in the reactor. Other examples of esterification reactions in which foaming occurs are the esterification of phthalic anhydride with 2-substituted alcohols like 2-ethyl hexanol and 2-propyl heptanol but also with unbranched and branched alcohols containing sodium soap contaminants particularly when the alcohol has been purified by treatment with sodium borohydride, the foaming problems are less if the alcohol has been purified by hydrofining or in which mixtures of such alcohols are used.

In a typical reaction, the acid or anhydride and the alcohol are preheated to an intermediate temperature and then the catalyst is introduced and the temperature rose to reaction temperature. Foam formation may start when the catalyst is introduced, causing enhanced reaction water formation and the temperature rose to the reaction temperature.

It has been proposed that foaming problems may be overcome by including an additional water entraining agent other than a reactant in the reaction or employing high operating pressures. However the use of such a water entraining agent introduces additional separation requirements and can also lead to impurities in the product. The use of higher pressures requires higher temperatures which does not help with the carry over problems. Thus, there remains a need for improvements in processes for the production of esters. Embodiments of the invention provide solutions to address these problems.

SUMMARY OF THE INVENTION

In a class of embodiments, the invention provides for a process for production of $C_4$ to $C_{15}$ esters by the esterification of a carboxylic acid or anhydride with a $C_4$ to $C_{15}$ alcohol comprising forming a reaction mixture of the acid or anhydride and a $C_4$ to $C_{15}$ alcohol comprising a stoichiometric excess of the alcohol and bringing the mixture to reaction temperature by providing an energy supply to the reaction to cause the mixture to react wherein initially the energy supply is controlled to reduce foaming and optionally the energy supply is subsequently increased to enhance reaction time.

In any of the embodiments described herein, the mixture or reactants may be caused to react by an esterification catalyst by heating the mixture containing the catalyst at a temperature in the range of from 200° C. to 250° C.

In any of the embodiments described herein, the process may comprise a greater stoichiometric excess of the alcohol.

In any of the embodiments described herein, the catalyst may be added after the mixing of the acid or anhydride and the alcohol and at a predetermined mixture temperature above the initial temperature of the mixture.

In any of the embodiments described herein, the heat input to the reaction may be reduced from the moment of catalyst injection to between 70 and 80% of the heat required for the optimum reaction at the reaction temperature.

In any of the embodiments described herein, after most of the reaction water has been removed, the energy input may be increased by increasing heating and/or stirring to speed up completion of the reaction.

In the embodiment described above, energy input may be increased after the esterification reaction is 70% complete.

In any of the embodiments described herein, the ratio of reflux flow rate in mol/min to the final batch size in mol times 60 may be in the range of 0.1 to 5 $hr^{-1}$.

DETAILED DESCRIPTION

Figure 1:
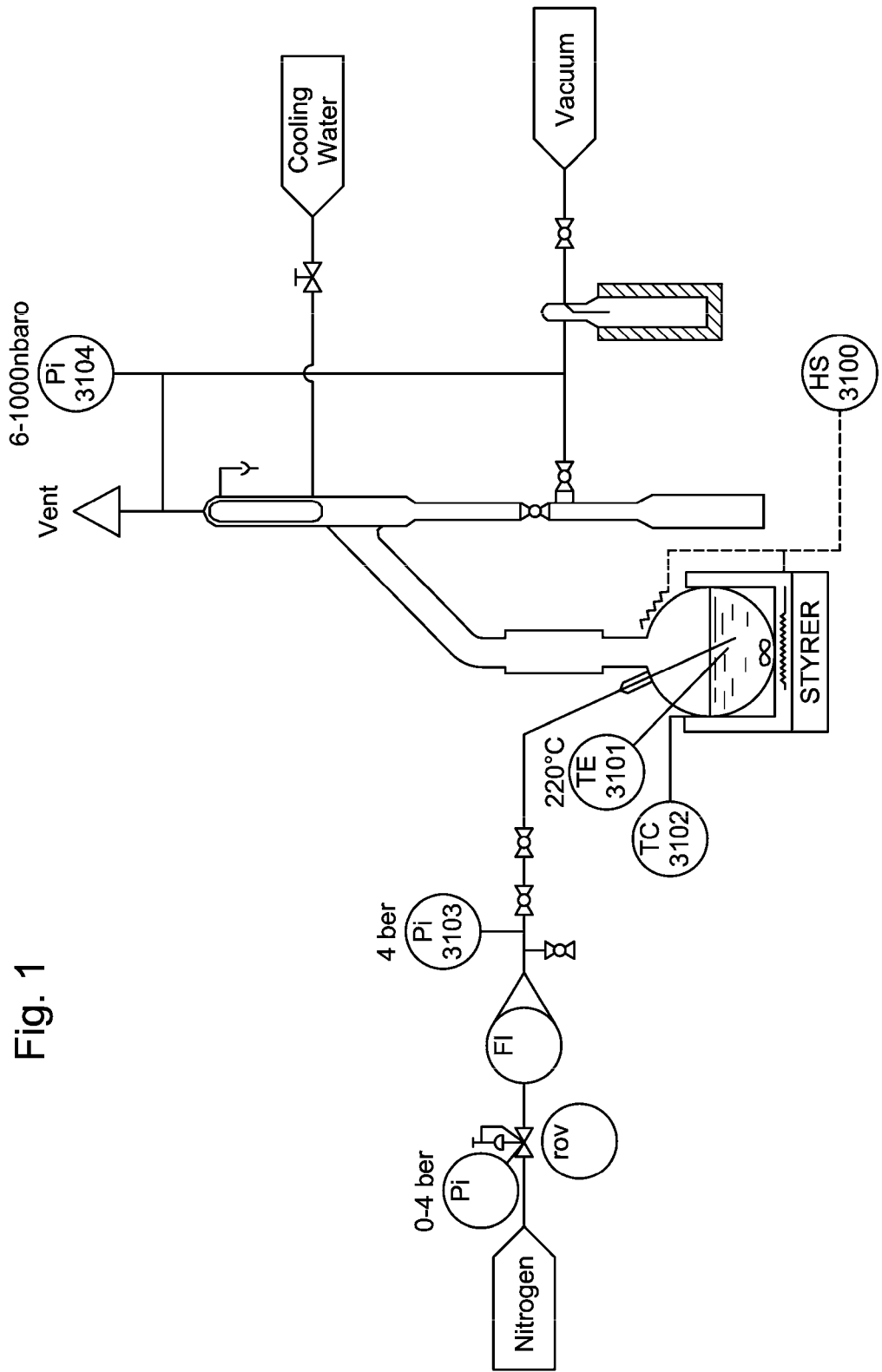
FIG. 1 shows the laboratory apparatus used in the Examples.

Before the present compounds, components, compositions, and/or methods are disclosed and described, it is to be understood that unless otherwise indicated this invention is not limited to specific compounds, components, compositions, reactants, reaction conditions, or the like, as such may vary, unless otherwise specified. It is also to be understood that the terminology used herein is for the purpose of describing particular embodiments only and is not intended to be limiting.

It must also be noted that, as used in the specification and the appended claims, the singular forms "a," "an" and "the" include plural referents unless otherwise specified.

Several classes of embodiments of the invention relate to improvements in or relating to esterification processes and in particular to esterification processes of acids and anhydrides with alcohols, particularly for the production of esters of phthalic acid and anhydrides, adipic acid, trimellitic, cyclohexane carboxylic acids and benzoic acid and $C_4$ to $C_{15}$ alcohols and, especially, the esterification of benzoic acid to produce benzoates. Such esters are particularly useful as plasticizers for polyvinyl chloride (PVC) compositions. The esters may be produced by the catalysed reaction of benzoic acid with an excess of the alcohol.

Surprisingly, we have found that the foaming may be reduced without significantly impairing reaction cycle time if the energy input or supply to the reactor is reduced during the initial phase of the reaction at reaction temperature when large amounts of water are being produced by lowering the heat supplied and optionally lowering the stirring energy. The energy input can be increased later in the reaction as the reaction proceeds and less water is produced.

Several embodiments of the invention therefore provide a process for the production of $C_4$ to $C_{15}$ esters by the esterification of a carboxylic acid or anhydride with a $C_4$ to $C_{15}$ alcohol comprising forming a reaction mixture of the acid and a $C_4$ to $C_{15}$ alcohol comprising a stoichiometric excess of the alcohol and bringing the mixture to reaction temperature by providing an energy supply to the reaction to cause the mixture to react wherein initially the energy supply is controlled to reduce foaming and optionally the energy supply is subsequently increased to enhance reaction time.

The energy input or supply may be thermal or mechanical energy or any other suitable for of energy and may be reduced in any suitable manner. Typically, the heat input is reduced and/or mechanical energy input such as stirring may be reduced. In an embodiment, we prefer to reduce heat input and optionally stirring.

The extent to which the energy input should be reduced depends upon the nature of the reactants; however, we have found that if the heat input is reduced to below that required for optimum reactivity foaming can be reduced without an undesirably large increase in reaction time.

For example, we have found that in the esterification of benzoic acid or anhydride with a $C_{10}$ alcohol if the heat input to the reaction is reduced from the moment of catalyst injection to between 70 and 80% of the heat required for the optimum reaction at the reaction temperature and optionally, the reduced heat is applied until at least 70% of the benzoic acid has been converted to a $C_{10}$ benzoate the problems of foaming are substantially eliminated or mitigated. We have also found that although this reduction in the heat input increases the reaction time, the balance between reducing foaming and increasing the reaction time is economically favourable. Similar benefits may be achieved in other esterification reactions such as in the production of phthalates, adipates, cyclohexanoates and trimellitates and the optimum energy reduction and duration of energy reduction can vary depending upon the reactants but it can be determined by simple experimentation.

In a preferred embodiment, the mixture of reactants is caused to react by an esterification catalyst by heating the mixture containing the catalyst at a temperature in the range of from 200° C. to 250° C., more preferably the reaction is performed at a temperature in the range from 205° C. to 225° C. The reaction mixture is also stirred at this temperature. Titanates are preferred catalysts and they typically become active at around 210° C. and reaction water is generated rapidly at this temperature.

In another embodiment, we use a greater stoichiometric excess of the alcohol as this decreases the boiling point of the mixture which enables the reaction to be performed at higher pressures than the conventional pressures and at lower temperatures. In several embodiments, "excess" refers to any value more than the stoichiometric amount to run a chemical reaction, for example, an esterification process. In several embodiments, "greater stoichiometric excess" refers to 1% or more, alternatively, 2% or more, alternatively, 5% or more, alternatively, 10% or more, alternatively, 15% or more, alternatively, 20% or more, and alternatively, 25% or more, of the "excess" as defined above. Surprisingly, these conditions enable effective removal of the water formed in reaction by boil up of the alcohol water mixture and it further reduces the carry over in the reflux of the acid and/or the ester formed in the reaction. The excess alcohol also pushes the reaction towards completion. In an embodiment, we prefer to use from 20 to 35 mole % excess alcohol. In a further embodiment, the invention is applied to esterification reactions in which the alcohol has been purified by treatment with sodium borohydride where foaming problems can be more acute. It is however also applicable to reactions in which the alcohol is purified by hydrofining or to processes in which mixtures of such alcohols are used.

The temperature of the mixture ("mixture temperature") when the catalyst is introduced is determined by the operator to suit the system employed. For convenience, this temperature is designated the "predetermined mixture temperature". The terms "predetermined mixture temperature", "desired esterification reaction temperature", and "initial temperature of the mixture" are used herein to indicate temperatures within temperature ranges that are known to be appropriate for a particular catalysed esterification reaction. For example, the desired esterification reaction temperature and predetermined mixture temperature will vary according to the nature of the reactants and the nature of the catalyst, and the invention does not concern these particular conditions but is concerned with the conditions that should be used depending on these particular temperature conditions.

Increasing the pressure in the reactor increases the difference in the boiling points of the reactants and the reaction product thus enhancing the ability to separate them under reflux. Furthermore, the increase in pressure ensures that the heat supplied to the reaction mixture is used for heating the reactants, rather than for vaporisation of the reactants. Within heat input limited equipment, this minimizes the time to reach the minimum desired temperature for the esterification reaction, which assures maximum achievable reaction rate. This in turn enables a reduction in reaction cycle time. In addition, the increased pressure and reduced vaporisation rate allow the predetermined mixture temperature, at which the catalyst is introduced, to be reached sooner, thereby further reducing the reaction time. Furthermore, since, during this initial stage of the reaction vaporisation of the reactants, particularly of alcohol, is substantially reduced, there is no requirement for reflux, thus avoiding the extra cooling effect of the refluxed material. Less alcohol in the vapour phase and in the overhead reflux system also means more alcohol in the reactant liquid mixture, which by its higher alcohol concentration assures a higher reaction rate again.

The catalyst should be added after the mixing of the acid or anhydride and the alcohol and at a predetermined mixture temperature above the initial temperature of the mixture. In an embodiment, the catalyst is added to the mixture when it is at a temperature in the range from 160° C. to 220° C., more preferably from 180° C. to 200° C.

The catalyst is generally added at a temperature below the desired esterification reaction temperature and, accordingly, after catalyst addition the temperature of the mixture is increased further to the desired esterification reaction temperature. Although the catalyst activity increases with increasing temperature, its stability decreases with increasing temperature and accordingly, depending on the nature of the catalyst, there is an optimum reaction temperature or a fairly narrow optimal temperature range. Irrespective of this temperature or range, addition of the catalyst causes the formation of more water at a faster rate which must be removed rapidly so that, with titanate catalyst, it has less chance of hydrolysing the water-sensitive catalyst. Traditionally, heat is continued to be supplied once the reaction temperature is reached, to promote the reaction, however we have found that if the energy supplied to the reactor which maybe heat and/or the intensity of the stirring is reduced once the reaction temperature was reached the level of foaming was reduced at least to the extent that any foam produced was confined to the reactor. The degree of reduction of energy input that is required depends upon the reactants. However, we have found that in the esterification of benzoic acid with a $C_{10}$ alcohol reducing stirring by about 50% and reducing the heat input to about 70% was successful in keeping the foam inside the reactor and in avoiding water flooding. Surprisingly, the rate of reaction and the total batch time were not significantly impacted by the use of the lower energy input at this stage of the reaction.

After most of the reaction water had been removed, when most of the limiting reagent has been converted to ester, the energy input could be increased by increasing heating and/or stirring to speed up completion of the reaction and we have found that this can be accomplished without foaming problems.

One or more of the starting materials, comprising the acid, the anhydride, or the alcohol and any recycle of the excess reactant, may be preheated before being mixed with the other reactant or before being introduced into the reaction vessel, such as up to a temperature of from 100° C. to 160° C. Oxygen may be removed from one or more of them, preferably from at least one of the fresh starting materials, to improve ester product colour. This oxygen removal occurs preferably after preheating and preferably by nitrogen stripping if it concerns a liquid, or by nitrogen purging of the equipment if it concerns a solid. These pre-treatments are preferably performed in a separate vessel before the starting material is introduced into the reactor vessel. The preheating reduces the reaction batch time, and performing the preheating and/or the oxygen removal in a separate vessel further reduces the time that a particular batch occupies the reactor and therefore also the overall reaction batch time. The invention therefore provides a process employing a particular energy input profile. The preferred profile depends upon the nature of the reactants and the relative quantities.

A variety of heating means may be applied to the esterification reactor to provide the controlled heat input. Many processes provide heat input by circulating a heating medium through one or more heating coils provided in the reactor, preferably under the liquid level, and/or through a heating mantle around the reactor wall. We have found that steam heating is more effective in transferring heat than hot oil, and we therefore prefer to provide heat input by steam, which preferably is at a pressure sufficiently high that it condenses at a temperature above the temperature of the reaction mixture. We prefer to use high pressure steam at a pressure of at least 40 barg (about 600 psig). The heat supplied may be controlled automatically by sensors within the reaction vessel or optionally in the heating medium circulation lines to effect the reduced energy input at the appropriate time.

We have found that, by applying and maintaining the pressure above atmospheric during the initial phase of the esterification reaction, water can be removed without the significant alcohol boil off that occurs in known processes which operate at atmospheric or reduced pressure in this initial phase. The use of the higher pressure reduces the need for alcohol recapture and recycle and hence increases the efficiency of the reaction. The use of increased pressure also maximises the usefulness of the heat supply into heating the reaction mixture, and results in the optimum reaction temperature being reached in a shorter time. It also keeps the reactant concentrations in the reaction mixture at the highest possible level. Both these factors result in a faster reaction rate.

In an embodiment, the esterification process is preferably performed initially under a blanket of inert gas such as nitrogen or methane. The pressure within the reactor, before any vapour vent is opened or vacuum system is commissioned; therefore, depends upon the pressure exerted by the inert gas combined with that exerted by the vapours within the reactor, which in turn depends upon the degree of reaction and the extent to which the reactants and the products of the reaction are vaporised, which in turn depends upon the temperature of the reaction. The temperature and therefore the pressure also depends upon the extent to which materials are refluxed. It is therefore preferred that the reactor system be provided with a vent valve and also a gas supply whereby gas may be introduced to increase the pressure within the reactor.

As reactor temperature and pressure increase, a vapour cloud of condensibles, i.e. primarily water but accompanied by some of the lighter boiling reactant, develops above the reactor liquid and displaces the inert gas that filled the reactor initially. The inert gas is pushed into the overhead system, and at a certain moment, the vapour cloud of condensibles reaches the reactor overhead condenser. At that time condensation typically starts, and liquids collect in the overhead separator. Depending on the initial liquid level in the overhead separator, sooner or later the liquid will overflow and the reflux of lighter boiling reactant to the reactor may be activated. We have found there is a tendency for the temperature of the reaction mixture to drop once the reflux system is activated. This in turn leads to a reduction in the pressure within the reactor. We have found that it may be particularly beneficial to introduce uncondensible gas into the reactor at this time to bring the pressure back up to at least re-establishing the desired conditions.

The vent and the gas supply may be provided at any suitable position in the reactor system which typically comprises reactant feed means, a reactor provided with heating means, a condenser, means for the separation of condensed materials, means for the recycle of reactants and means for reaction product removal. The vent and the gas supply may be provided in the reactor or elsewhere and we prefer that they are provided at or close to the condenser where it is most effective in impairing or stopping condensation which is typically still undesired at that time.

The reactor is provided with a mixer and, in the preferred reaction cycle, the fresh alcohol feed is introduced into the reactor until a minimum level is reached. At this stage, the mixer is activated and introduction of the acid, such as benzoic acid, is instigated; further alcohol consisting of fresh alcohol or recycle alcohol may also be introduced. Reactor heating may be implemented at this time, preferably as soon as the liquid level in the reactor reaches the surface of the heating equipment.

The reactor system is also provided with means for the introduction of the catalyst into the reaction mixture, preferably, introducing the catalyst below the surface of the stirred reaction mixture. The means must be such that the catalyst can be introduced into the reactor when it is under superatmospheric pressure. It is therefore preferred that the catalyst be injected into the reactor by means of pressure of the inert gas that is used as the blanket for the reaction. It is also preferred that after the catalyst is injected, the catalyst injection system be flushed with at least one of the reactants. In particular, where the esterification comprises the reaction of an acid or anhydride with an alcohol, we prefer that the catalyst injector be flushed with the alcohol. When the catalyst is water sensitive, such as with titanium catalyst, it is preferred that the reactant used for flushing has a low water content, such as at most 500 ppm by weight, preferably at most 200 ppm by weight, most preferably at most 100 ppm by weight. After introduction of the catalyst the temperature is raised to the reaction temperature, typically from 210° C.-225° C. In this embodiment, once the reaction temperature is reached, the energy input to the reaction mixture is reduced by lowering the heat input and, optionally also reducing the degree of stirring.

The techniques of the present invention are particularly useful when used in combination with other techniques that are known for improving the efficiency of esterification reactions. In particular, the techniques may be used with other techniques that are known for minimising contact between water and the esterification catalyst. For example, the reaction system may include a reflux drier column, such as is described in U.S. Pat. No. 5,324,853. A reflux column or drier serves to heat and dry the condensed alcohol as it is being refluxed for recycle to the reaction, preferably, by using hot vapours from the reactor as heating medium. As an alternative, the cold condensed alcohol from the overhead collector may be heated and flashed to remove most of the water as vapour, and the flashed liquid may then be refluxed to the reactor, optionally, routed through a reflux drier column to achieve even lower water levels. Another useful technique is described in WO2008/110306, in which the catalyst is introduced into the reaction mixture below the surface of the liquid reaction mixture. This may be accomplished by the injection of the catalyst through a probe whose opening is below the surface of the liquid reaction mixture. In this way, contact between the catalyst and any water rich vapour in the atmosphere above the liquid reaction mixture may be minimised and the catalyst stability preserved. It is also preferred that after the catalyst is injected, the catalyst injection system be flushed with at least one of the reactants.

We have found that reflux drying improves reaction batch time because of the lower water content and the higher temperature of the reflux. This reduces the amount of heat required to revapourise the water in the reflux and required to heat the colder reflux up to the reaction temperature. We have also found that a larger size reflux drier column allows a steeper pressure profile due to the lower pressure drop in the vapour flowing to the reactor overhead system. We have also found that, in case the reflux drier column cross section is causing an excessive pressure drop, a partial vapour bypass over the drier column may alleviate this problem and help reaching higher reactor productivities whilst the reflux continues to be adequately dried.

In an embodiment, we prefer that the esterification processes be performed in the manner described in WO 2008/110305, wherein the esterification recipe and the feed pretreatment are optimised in order to optimise the reaction rate and to reduce reaction time. A particularly preferred reaction cycle for the production of esters and in particular plasticiser esters comprises this feed recipe adjustment and pre-treatment followed by the employment of the reaction process of embodiments of the present invention, followed by the neutralisation technique of WO2006/125670 and the purification techniques of WO2005/021482. The preferred cycle of the present invention depends upon the nature of the reactants and the catalyst. In the preferred cycle, alcohol is preheated to a temperature in the range from 100° C. to 160° C. This preferred preheating temperature is grade dependent, because of the change in boiling point. Excessive preheating is to be avoided in order to keep alcohol vapour losses from the preheating step within acceptable limits. For $C_7$ alcohol we prefer to preheat from 100° C. to 115° C., for $C_9$ and $C_{10}$ alcohol we prefer from 130° C. to 150° C., and for $C_{11}$ or higher, such as isotridecyl alcohol, we prefer from 130° C. to 155° C. or even 160° C. The preheated alcohol is then preferably added to a reaction vessel that is blanketed with an inert gas preferably nitrogen or methane and is heated at a temperature in the range from 120° C. to 150° C. or 160° C. and is at atmospheric pressure. Maximum heat input to the reactor is preferably applied as soon as possible. The acid or acid anhydride is then added at a temperature in the range from 135° C. to 160° C. or even up to 180° C. The content of the reaction vessel is then rapidly heated to the predetermined mixture temperature at which the catalyst is added.

Until the desired esterification reaction temperature is reached, the pressure of the reaction vessel should be maintained at a level sufficient to distil off the water whilst preventing significant alcohol boiling while forming an ester from the reactants. The pressure of the reaction vessel is generally adjusted continually to ensure continuous vaporisation and removal of water. Typically, the initial reaction pressure is close to atmospheric pressure, for example 1 to 2 bara (101.3 to 202.6 kPa), and moves through a maximum, when the desired esterification reaction temperature or the lower end of the optimal range is reached, of for example 1.5 to 2.5 bara (152.0 to 253.2 kPa), and then reduces toward an increasing vacuum as the reaction proceeds. Preferably, the final reaction pressure ranges from 2 bara (202.6 kPa) to 100 mm Hg absolute (13.3 kPa). More preferably, the final reaction pressure ranges from 1.0 bara (101.3 kPa) to 150 mm Hg absolute (20 kPa). Most preferably, the final reaction pressure ranges from 190 mm Hg absolute (25 kPa) to 350 mm Hg absolute (46.7 kPa), typically 30-31 kPa. Once the desired esterification reaction temperature is reached the energy input to the reaction mixture is reduced to a level below the optimum level for reactivity to reduce the foaming tendency of the mixture.

The total amount of catalyst that should be used is determined primarily by four factors. First, the total reaction rate generally increases as the amount of catalyst, typically, expressed in weight percent of catalyst per weight of limiting reactant, increases up to a certain optimal concentration. The reaction rate also depends on the particular catalyst activity, the reaction temperature, and the water content of the reaction mixture. A relatively high concentration of catalyst may result in the organometallic complex esterification catalyst reacting with itself, to form unreactive agglomerated catalyst. Furthermore, a relatively higher concentration of certain esterification catalysts can cause product haze formation. In addition, process economics dictate that beyond an optimal point, further catalyst addition is not economical. If the reaction mixture contains an appreciable amount of certain cationic species, then the catalyst requirement must be increased to reach a desired reaction rate. The amount of catalyst used will therefore be chosen having taken all these factors into consideration.

When no reflux drying is performed but even when a reflux drier and/or flash step is provided, stopping the reflux to the reactor before the end of the run is reached, drives the reaction faster to completion because no more water is returned to the reactor and at the same time the amount of excess reagent in the crude ester is reduced, such as down to 12-15% wt, thereby reducing the volume of crude ester to be further processed and the amount of excess reagent that needs to be removed in the downstream finishing steps. In embodiment, we therefore prefer to stop the reflux at least 2 minutes, preferably at least 5 minutes, more preferably at least 7 minutes and even more preferably at least 10 minutes and even 15 minutes before the expected batch termination time. We have found that when the alcohol reflux is continued till the end of the batch and through a reflux drier, the water content of the crude ester at the end of the reactor run may still be as high as 50 ppm wt. When stopping the alcohol reflux about 12 minutes before the end of the batch termination time, the water content of the crude ester may be only 20 ppm by weight, or may even reach 10 ppm wt or below. We have found that the presence of water, even in these small amounts, may have a surprisingly large effect on the rate of the reaction at the end of run, and therefore on the completion of the reaction and on the total batch time.

When the reflux to the reactor, or to the reflux drying step, is stopped, the alcohol coming from the overhead collection drum is routed to the recycle alcohol tank. Employing the techniques several embodiments of the present invention have been found to reduce the amount of acid or ester carried over in the reflux alcohol thus resulting in a purer product and requiring less separation techniques. When the batch is to be terminated, heat input to the reactor is stopped and the vacuum is broken, preferably by allowing nitrogen into the reactor system, more preferably into the reactor overhead system. This breaking of the vacuum is considered the moment of termination of the batch. As soon as the vacuum is broken, the reactor content may immediately be evacuated to a collection vessel in and from which it may be further processed. In case the next batch of product is of the same quality, the reactor is then ready for starting the new batch.

The esterification process of the present invention may also include one or more of the following steps: removal of excess reagent by nitrogen or steam stripping; addition of adsorbents such as alumina, silica gel, activated carbon, clay and/or filter aid to the reaction mixture following esterification before further treatment. In certain cases, adsorbent treatment may occur later in the process, following stripping, and in still other cases the adsorbent step may be eliminated from the process altogether. Addition of water and base to simultaneously neutralize the residual organic acids and hydrolyze the catalyst (if present); filtration of solids from the ester mixture containing the bulk of the excess reagent (acid or alcohol) used in the esterification process; removal of the excess reagent from the ester mixture by, for example, steam or nitrogen stripping under vacuum and recycling of the excess reagent to the reaction vessel; and, removing solids from the stripped ester in a final filtration, may also be included in the process.

Esterification catalysts that may be used include acid catalysts and organometallic catalysts. Organometallic esterification catalysts are preferred and include titanium, zirconium and tin catalysts such as titanium, zirconium and tin alkoxides, carboxylates and chelates. See U.S. Pat. No. 3,056,818. Titanium alkoxides are useful.

Typical titanium alkoxides which can be used as catalysts include tetramethyl titanates, tetraethyl titanates, tetrapropyl titanates, tetra-isopropyl titanates, tetrabutyl titanates, tetrapentyl titanates, tetrahexyl titanates, tetraheptyl titanates, tetra-octyl titanates, tetranonyl titanates, tetradecyl titanates including tetra-2-propylheptyl titanate, tetradodecyl titanates, tetrahexadecyl titanates, tetra-octadecyl titanates, tetraphenyl titanates, and mixtures thereof. The alkoxy groups on the titanium atom can all be the same or they can be different, and their alkyl chains may be normal and/or branched, or mixtures thereof. The tin or zirconium counterparts of the above alcoholates can be substituted in whole or in part as catalysts. Tetra-isopropyl titanate (TIPT) is very suitable. Tetra-isooctyl titanates (TIOT) are also useful.

Methods according to the present invention are capable of forming plasticizer phthalates, benzoates, cyclohexanoates, adipates and trimellitates from $C_4$ to $C_{15}$ alcohols, preferably $C_9$ to $C_{13}$. Preferred alcohols include hexanol, heptanol, isoheptanol, 2-ethyl-hexanol, nonanol, isononanol and mixtures of branched chain nonanols, linear and branched chain decanols, including 2-propyl-heptanol such as those available from Evonik and BASF, normal and/or branched undecanol and tridecanol. Because of the increase in the rate of reaction, in accordance with this invention, the process is particularly useful in esterifications catalyzed by titanium, zirconium, or tin organometallic catalysts.

The preferred acid or anhydride component comprises phthalic acid or anhydride, trimellitic acid or anhydride, aromatic carboxylic acids such as benzoic acid, cyclohexane mono- or poly carboxylic acids and adipic acid or anhydride.

The esters produced by the present invention are particularly useful as plasticizers for polyvinyl chloride (PVC), particularly the phthalates, cyclohexanoates, adipates, trimellitates and benzoates. In particular $C_9$ to $C_{11}$ alkyl benzoates, due to their high boiling range (>290° C.) and low viscosity, will have very little contribution to the VOC's emitted from finished polyvinyl chloride products. In particular the $C_{10}$ alkyl benzoate with a boiling point above 315° C. can be incorporated into polyvinyl chloride compositions with no contributions to the VOC emissions in the finished product. The total VOCs, as measured by the Field and Laboratory Emission Cell (FLEC), are defined as the integrated detector response in toluene equivalents of compounds eluting between and including hexane (n-$C_6$) and hexadecane (n-$C_{16}$) (Europe standard) or octadecane (n$C_{18}$) (Norden countries [Norway, Sweden] standard). We have also found that $C_9$ to $C_{11}$ alkyl benzoates are particularly versatile when used as plasticisers and/or viscosity depressants in polyvinyl chloride formulations. We have found that the use of the alkyl benzoates brings benefits in a wide range of applications. U.S. Pat. No. 7,629,413 is concerned with the use of $C_9$ to $C_{11}$ alkyl benzoates as plasticisers.

The present invention is particularly useful in the production of $C_9$ to $C_{11}$ alkyl benzoates and in particular $C_{10}$ alkyl benzoates which provide a plasticiser which can be incorporated into polyvinyl chloride compositions and will enhance the low temperature flexibility measured by the Clash and Berg test. We have also found that the use of a $C_{10}$ alkyl benzoate plasticiser in a 50/50 blend ratio with diisononyl phthalate, di-2-propyl heptyl phthalate or diisodecyl phthalate in a plastisol formulation containing 60 parts of plasticiser per 100 parts of polyvinyl chloride, lowers the Clash & Berg temperature by at least 9° C. as compared with a formulation based entirely on the corresponding phthalate.

The total plasticiser content of the polyvinyl chloride (PVC) composition may be made up of the $C_9$ benzoate and/or $C_{10}$ benzoate and/or $C_{11}$ benzoate and, if present, one or more plasticisers (termed herein "primary plasticisers") that are other than $C_9$ to $C_{11}$ benzoate(s). Thus, the total plasticiser content may be made up of one or more $C_9$ to $C_{11}$ benzoates only, without primary plasticiser. However, it is preferred that the total plasticiser content also includes one or more primary plasticisers in addition to the one or more $C_9$ to $C_{11}$ benzoates. Preferably the (total) plasticiser content of the PVC composition is from 20 to 150 parts by weight plasticiser per hundred parts by weight PVC (phr), more preferably 20 to 130 phr such as 40 to 130 phr, and most preferably 20 to 100 phr such as 40 to 100 phr. The particular proportions of $C_9$ to $C_{11}$ benzoate, primary plasticiser and PVC in the composition are selected on the basis of the particular plasticisers used and the target properties required for the end PVC composition.

The reduction in plasticiser content and the use of benzoate plasticisers, gives a product with excellent processing characteristics of low viscosity, and low emissions with good stain and wear resistance. By using the benzoate plasticisers it becomes much easier to formulate and obtain products that are intended for indoor use and that also do not elute in the FLEC region of the European ENV13419-3 standard and/or the Nordtest NT Build 438 standard.

The benzoate esters are particularly useful in the second layer of floor coverings is generally a foam decorative layer, which carries printing according to the desired appearance of the floor covering as is described in U.S. Pat. No. 7,629,413. They can also be used include rotational moulding, injection moulding and extrusion and in each instance the polyvinyl chloride formulation has desired properties which are provided through the nature of the polyvinyl chloride, the choice of plasticiser and the use of processing aids. As an example, in extrusion or calendaring the low viscosity and faster fusing obtained by the use of the $C_9$ to $C_{11}$ alkyl benzoates would allow for shorter dry blending time for the formulation.

When the $C_9$ to $C_{11}$ alkyl benzoate is a $C_{10}$ alkyl benzoate, the level of $C_{10}$ alkyl benzoate is preferably at least 50%, more preferably at least 70%, even more preferably at least 80 or 85% or even 88% by weight, again on the same basis, and not more than 97%, preferably not more than 95, 93, 91 or 90 wt %. Such $C_{10}$ alkyl benzoate may further comprise at least 3% by weight, preferably at least 5%, and more preferably at least 6% by weight $C_{11}$ alkyl benzoate. An advantageous $C_{10}$ alkyl benzoate may contain about 4 wt % $C_9$, 89 wt % $C_{10}$ and 7 wt % $C_{11}$ alkyl benzoate.

EXAMPLES

It is to be understood that while the invention has been described in conjunction with the specific embodiments thereof, the foregoing description is intended to illustrate and not limit the scope of the invention. Other aspects, advantages and modifications will be apparent to those skilled in the art to which the invention pertains.

Therefore, the following examples are put forth so as to provide those skilled in the art with a complete disclosure and description and are not intended to limit the scope of that which the inventors regard as their invention.

Embodiments of the present invention are illustrated by the following Examples that employed a laboratory esterification unit consisting of a 250 ml glass flask with three necks, a reflux column, a cooler, and a water/alcohol separator in which reaction water was collected. From the separator, condensed alcohol flowed back into the reaction flask through the reflux column. Heating was provided by means of an external electrical heater with a 156 Watt heating element. Stirring inside the reactor was assured by means of a magnetic stirring bar. The equipment employed a vacuum system. The vacuum system consisted of a vacuum pump, a buffer vessel, a pressure transmitter, and a vacuum control valve. The ratio of reflux flow rate in mol/min to the final ester batch size in moles at 100% acid conversion times 60 to convert into mol/hr is a useful factor for conversion of laboratory data to commercial reactors. We have found that this is preferably in the range of 0.1 to 5 $hr^{-1}$.

The reaction conditions were:

| Starting Conditions | | Diisononyl Phthalate Production | Decyl Benzoate Production |
|---|---|---|---|
| Phthalic anhydride | gram | 53.700 | — |
| | mole | 0.362 | — |
| Benzoic acid | gram | — | 70.900 |
| | mole | — | 0.581 |
| Isononyl alcohol | gram | 120.400 | — |
| | mole | 0.836 | — |
| Isodecyl alcohol | gram | — | 103.200 |
| | mole | — | 0.653 |
| Tetra Octyl Titanate | gram | 0.223 | 0.223 |
| | wt % | 0.128 | 0.128 |
| Total Reactor weight | gram | 174.323 | 174.323 |
| Excess alcohol | molar | 1.206 | 1.218 |
| Initial acidity (theor.) | mgKOH/g | 116.40 | — |
| Initial acidity (theor.) | mgKOH/g | — | 186.84 |
| Catalyst Injection at | ° C. | 185.00 | 185.00 |

All runs were carried out with 21.8% molar excess alcohol over the stoichiometric amount required to convert either benzoic acid or phthalic anhydride to the ester. To start, a run the separator was pre-filled with fresh alcohol. The reactor was loaded with the desired weight of benzoic acid or phthalic anhydride and with the required amount of alcohol corrected for the estimated amount of fresh alcohol returning from the overhead separator into the reactor upon the accumulation of the reaction water. One gram of alcohol was kept aside for the preparation of the catalyst injection solution. This small amount of alcohol was also included in the alcohol excess. The total mass added to the reactor was the same for all runs and was considered to simulate maximum filling of industrial reactors. A benzoate run contained 60% more acid functions and releases 60% more reaction water than diisononyl phthalate test for equal reactor filling. FIG. 1 shows the laboratory apparatus that was used.

Before starting any run the equipment was flushed with nitrogen and then the pressure was reduced to a starting pressure of 600 mmHg. The heater was then started. For the production of diisononyl phthalate, the heater was kept at maximum power for the entire reaction (156 Watt heating element).

The dissolved catalyst was introduced when the temperature inside the reaction zone is had reached 185° C. Typically, this happened 15 to 16 minutes after starting the heaters.

The desired reaction temperature (220° C.) was reached after about 30 minutes. Reaction water started to accumulate when the reaction temperature exceeded 210° C. As the reaction progressed and the average molecular weight of the reactor mixture became heavier, it was necessary to decrease the pressure stepwise to keep the reaction temperature constant and to maintain a steady alcohol reflux.

At regular time intervals, about every 10 minutes after catalyst injection, liquid samples were withdrawn from the reactor and analyzed for residual acidity. Target end-acidity was 0.05 mg KOH/g. The final crude ester and the recycle alcohol collected in the separator and were analyzed by GC for total acidity. The reaction water was analyzed for total acidity.

The overhead separator had a total volume of about 50 ml, whereas only 10 ml of reaction water had to be collected. The majority of the alcohol in the upper layer of the separator did not participate in the reaction. Entrainment of ester and acid into the overhead separator resulted in accumulation of non-reacted acid in the large stagnant alcohol layer. By adding glass beads, the void volume of the separator was reduced to 20 ml, assuring a rapid turn-over of the reflux alcohol into the reaction zone. With this set-up, no appreciable non-reacted acid remained in the recycle alcohol by the end of a batch test. The disadvantage was that the water accumulation rate could no longer be monitored due to the presence of the glass beads in the calibrated part of the separator.

The production of the benzoate ester was more sensitive to foam formation than the production of diisononyl phthalate and diisodecyl phthalate. Foaming was observed shortly after the reactor temperature exceeded 210° C. and coincided with the formation of free reaction water. The foam rapidly flooded the reflux tower and over-flowed into the separator. The hot foam heated up the top layer in the oil/water separator causing boil-up and return of reaction water into the reactor where it caused severe disturbance of the steady boiling regime. Once the process became unstable, it was difficult to recover steady state operation.

It was found that foam formation inside the reactor and flooding of the reflux tower could be prevented by a combination of reduced stirring rate and reduced heat input when approaching and initially at the operating temperature.

Figure 2:
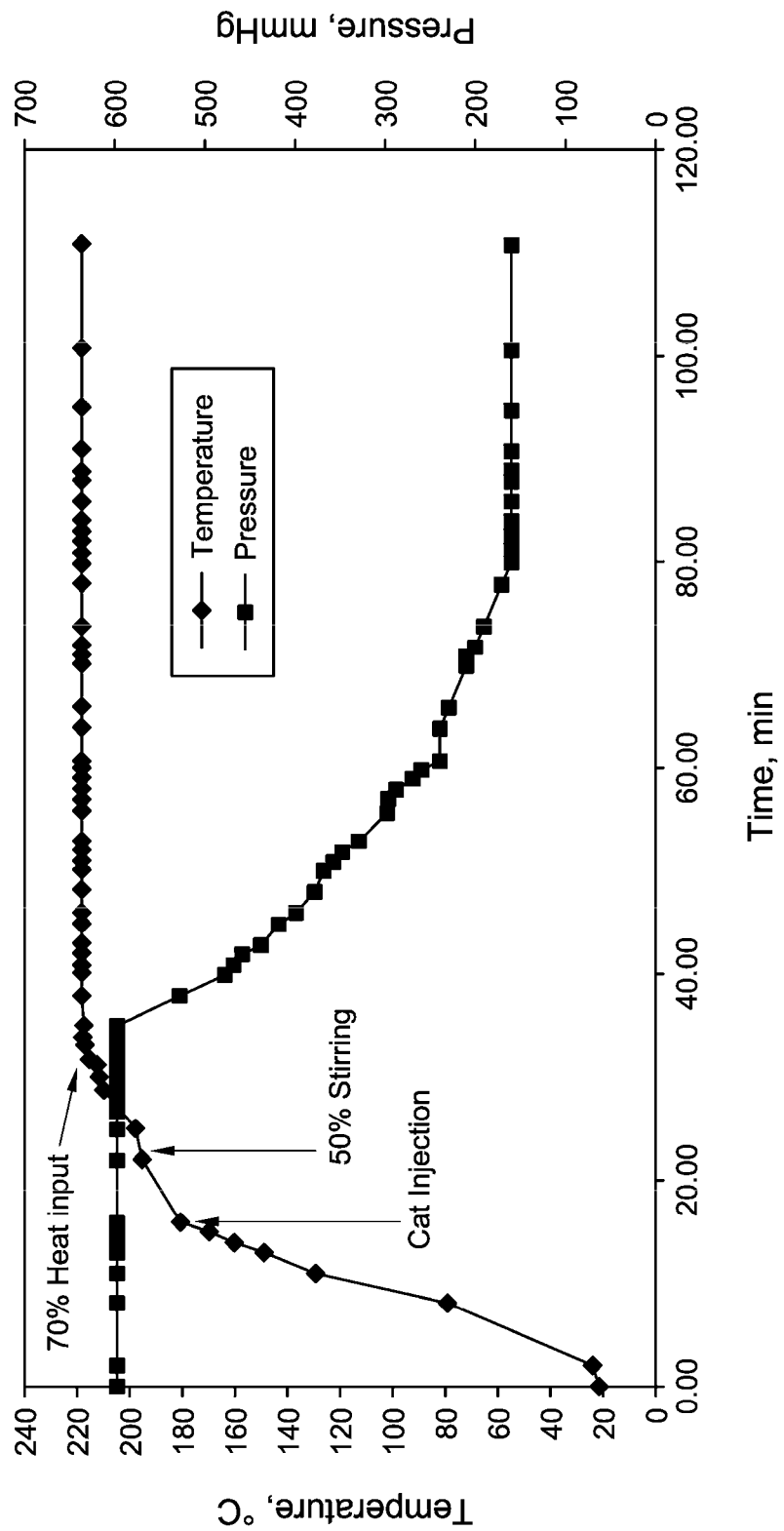
FIG. 2 shows the pressure and temperature profile during a reaction for the manufacture of a $C_{10}$ benzoate.

In a first experiment, the esterification of benzoic acid with the $C_{10}$ EXXAL™-10 Alcohol (available from ExxonMobil Chemical, Houston, Tex.), stirring was turned down to 50% and heat input was decreased to 70% of maximum once the reactor temperature had reached 215° C. This reduced the foaming intensity and the foam did not flood the tower. No heavy boil-up inside the reactor due to a return of reaction water was observed. Throughout the entire test, a continuous alcohol reflux could be established and maintained. The batch time needed to achieve end-acidity was marginally influenced. FIG. 2 shows the pressure and temperature profiles for the manufacture of the $C_{10}$ benzoate during this experiment.

A comparative experiment with full heat input at 50% stirring was unstable. Another run with full heat input but 50% catalyst load was also unstable and required a much longer batch time to achieve the target end-conversion.

Figure 3:
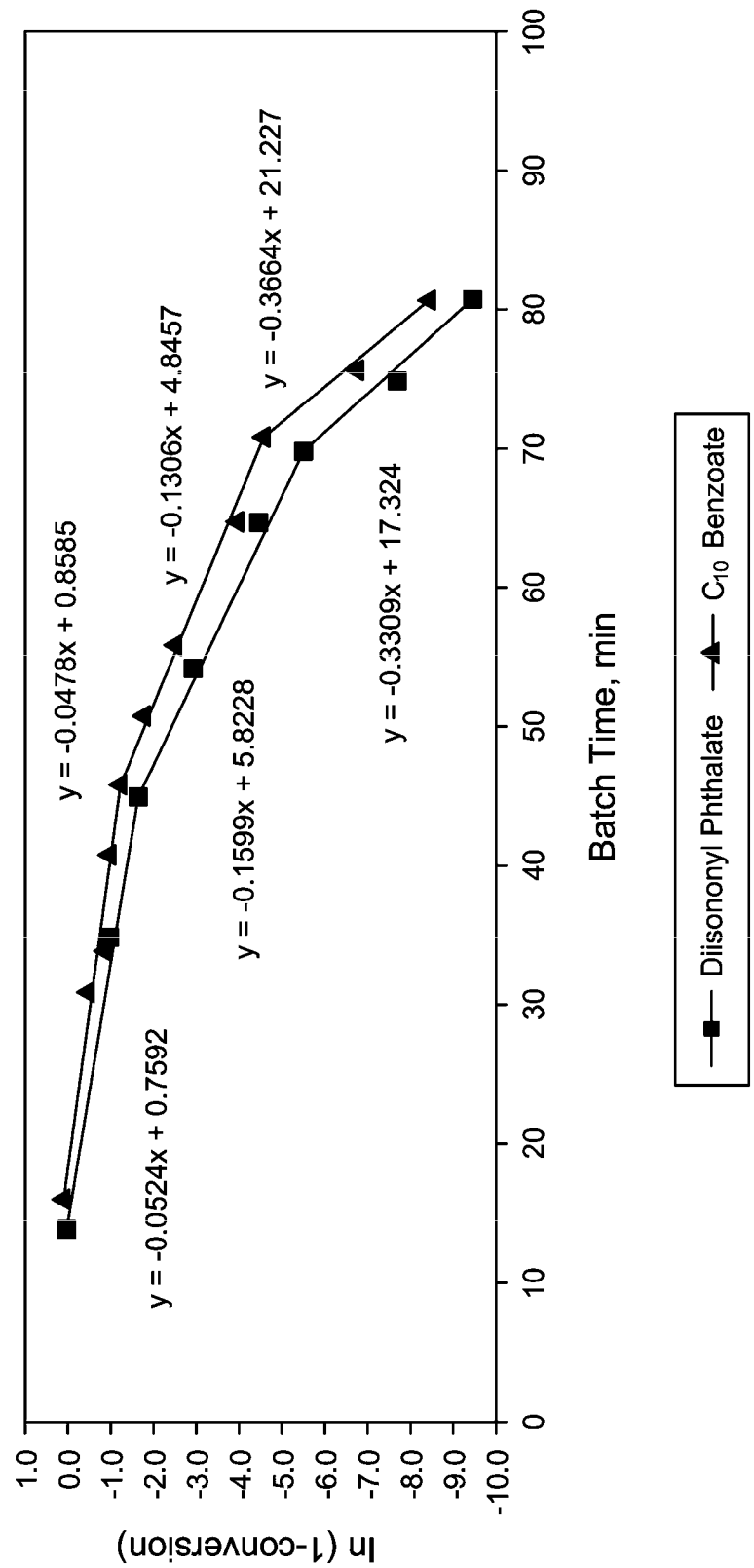
FIG. 3 shows the conversion profiles of the esters produced in the Examples.

In spite of the higher amount of water to be removed for the $C_{10}$ benzoate run as compared to the DNP run, both the benzoate (at 70% heat input) and phthalate (at 100% heat input) experiments achieved target acidity of 0.05 mg KOH/g between 80-90 minutes. FIG. 3 shows the conversion profiles in a semi-log plot versus time. For both runs, the rate derived from $1^{st}$ order and tended to increase towards the end of the esterification. Both runs followed a similar conversion pattern, proving they were controlled by the same constraints, most probably the level of dissolved water along the reaction. In FIG. 3, the squares are the values for diisononyl phthalate and the triangles for $C_{10}$ benzoate.

Figure 4:
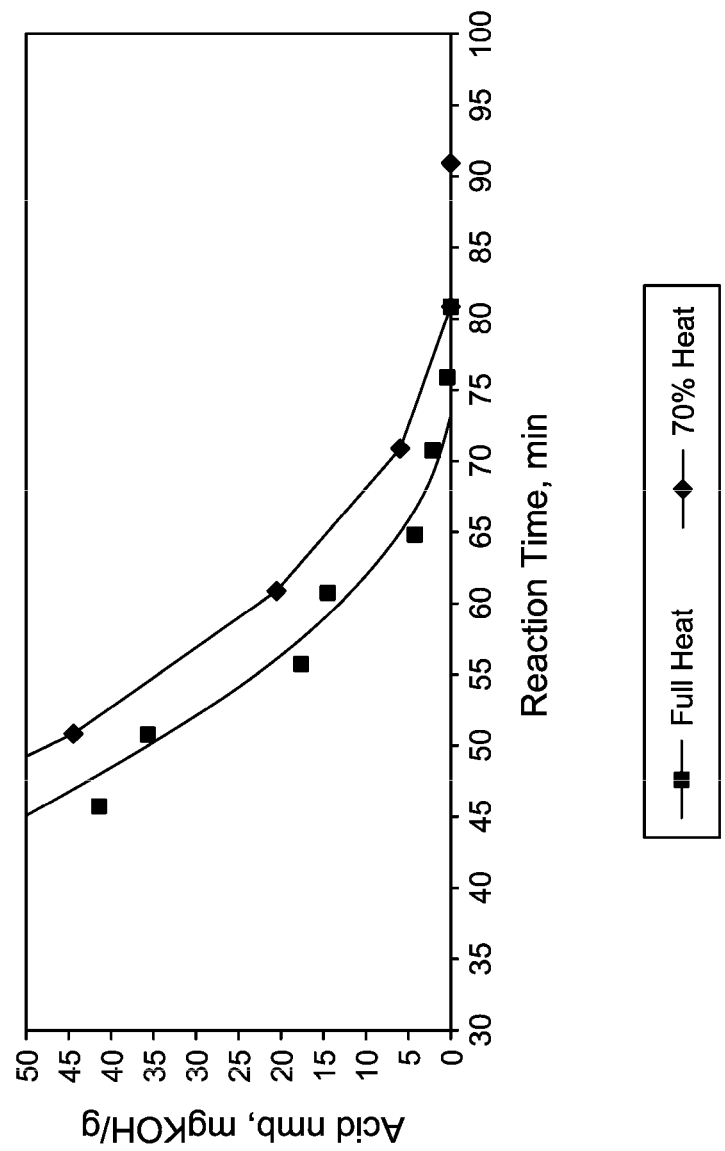
FIG. 4 shows a comparison of the acid number profiles of the Examples at 70% and 100% heat input.

FIG. 4 shows the comparison of the acid number profiles of the experiments at 70% heat input without foaming (diamonds) and 100% heat input with foaming (squares) in the production of a $C_{10}$ benzoate.

Figure 5:
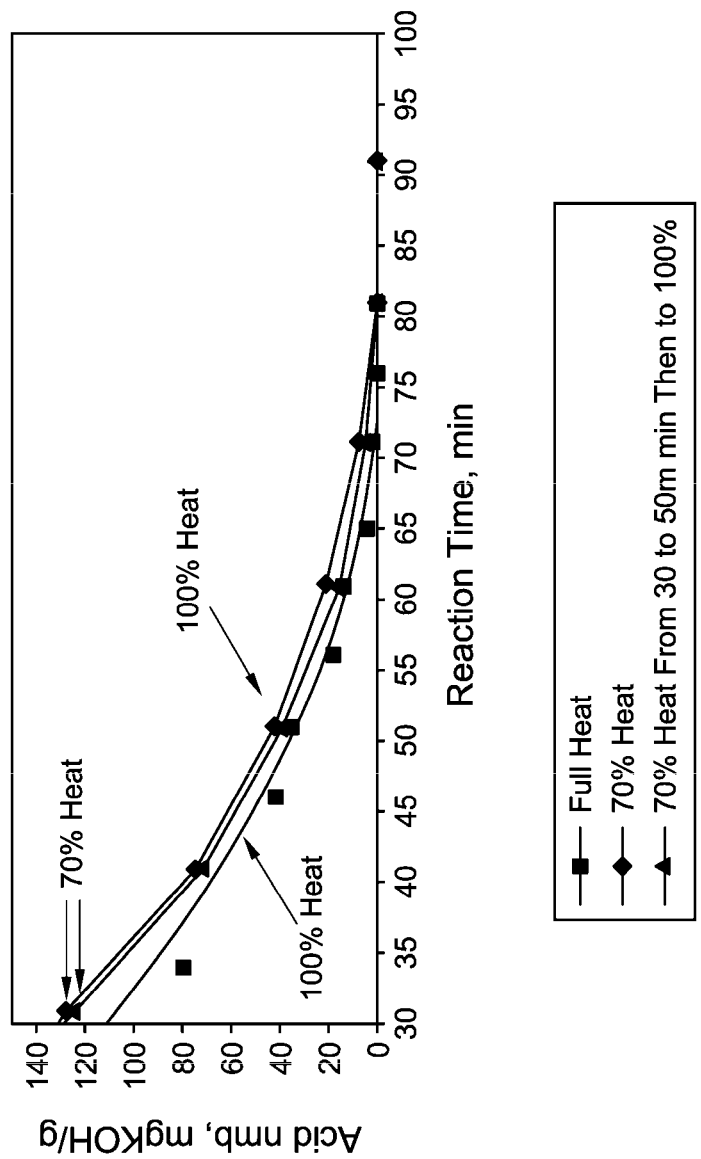
FIG. 5 shows the acid profiles of the Examples.

Further optimization appeared possible by restoring full heat input into the reaction once the majority of the water had been removed. A run was set up with 70% heat input as from 215° C. until about 80% of the reaction water was recovered (between 30 and 50 min), after which the heat input was restored to 100%. Restoring full heat capacity was feasible without causing foaming issues and resulted in some rate increase, approaching the run with maximum heat input, compared to the experiment which was kept at 70% heat all the time. FIG. 5 shows the acid profiles.

Further experiments were performed in modified equipment in order to obtain a more quantitative measurement of the impact of lower heat input on the alcohol reflux rate.

To be able to measure the alcohol reflux rate, a calibrated overhead separator was connected by its bottom valve to the reaction zone employed in the previous examples such that the alcohol could flow back continuously without being held up in the separator and hence without compositional changes of the reactor content. For each rate measurement, the reflux was given about 30 minutes to stabilize and then a measurement was carried out by closing the separator bottom valve and measuring the amount of reflux alcohol accumulating in the calibrated boot of the separator in one minute.

Three measurements were made and the average was taken as the corresponding reflux rate. The effect of reducing the heat input during the reaction at reaction temperature was studied for three levels of benzoic acid conversion. Blends of benzoic acid, isodecanol and isodecyl benzoate were prepared aiming at mixtures representing 35%, 75% and 100% of benzoic acid conversion respectively. All compositions had the same amount of equivalent benzoic acid (0.58 mole) and 28 mole % excess of isodecanol over benzoic acid. No catalyst was added to avoid reaction and to keep a constant composition. Each composition was evaluated at 100% (or 156 W), 85%, 75% and 70% heat input of the heat input required for optimum reaction rate. Operating pressure was adapted to achieve steady alcohol reflux at 220° C. for the given compositions.

The results are shown in the following table.

TABLE 1

Isodecanol reflux rate for Benzoic Acid esterification - Effect of heat input

|  |  | 33% conversion case | 74% conversion case | 100% conversion case |
|---|---|---|---|---|
| Benzoic Acid, | gram | 47.50 | 17.70 | 0.00 |
|  | mol | 0.39 | 0.15 | 0.00 |
| Isodecanol, | gram | 87.00 | 51.10 | 28.00 |
|  | mol | 0.55 | 0.32 | 0.18 |
| Isodecyl benzoate, | gram | 50.20 | 114.40 | 152.00 |
|  | mol | 0.19 | 0.44 | 0.58 |
| Heat up time to 220° C. at 156 W (100% heat), | min | 24.00 | 24.00 | 26.00 |
| Reflux pressure at 156 W (100% heat), | mmHg | 420.00 | 315.00 | 197.00 |
| Isodecanol reflux rate at 100% heat, | ml/min | 3.84 | 4.80 | 5.70 |
|  | mol/min | 0.0243 | 0.0304 | 0.0361 |
| Ratio reflux rate to batch size | hr-1 | 2.514 | 3.143 | 3.732 |
| Isodecanol reflux rate at 85% heat, | ml/min | 2.53 | 2.90 | 4.80 |
|  | mol/min | 0.0160 | 0.0184 | 0.0304 |
| Ratio reflux rate to batch size | hr-1 | 1.656 | 1.899 | 3.143 |

TABLE 1-continued

Isodecanol reflux rate for Benzoic Acid esterification - Effect of heat input

| | | 33% conversion case | 74% conversion case | 100% conversion case |
|---|---|---|---|---|
| Reflux pressure at 117 W (75% heat), | mmHg | 350.00 | 305.00 | 197.00 |
| Isodecanol reflux rate at 75% heat, | ml/min | 0.84 | 1.70 | 3.60 |
| | mol/min | 0.0053 | 0.0108 | 0.0228 |
| Ratio reflux rate to batch size | hr-1 | 0.550 | 1.113 | 2.357 |
| Reflux pressure at 109 W (70% heat), | mmHg | 315.00 | 300.00 | 199.00 |
| Isodecanol reflux rate at 70% heat, | ml/min | 0.67 | 1.00 | 2.70 |
| | mol/min | 0.0042 | 0.0063 | 0.0171 |
| Ratio reflux rate to batch size | hr-1 | 0.439 | 0.655 | 1.768 |

The results indicate that a reduction of the heat input to 70% avoids foaming upsets and decreased the alcohol reflux rate to about 20%. In spite of the dramatic decrease in alcohol reflux rate which coincided with the reduction of the heat input, the reaction rate would be decreased by only 20% and the total batch time would be increased by only 10 minutes.

Figure 6:
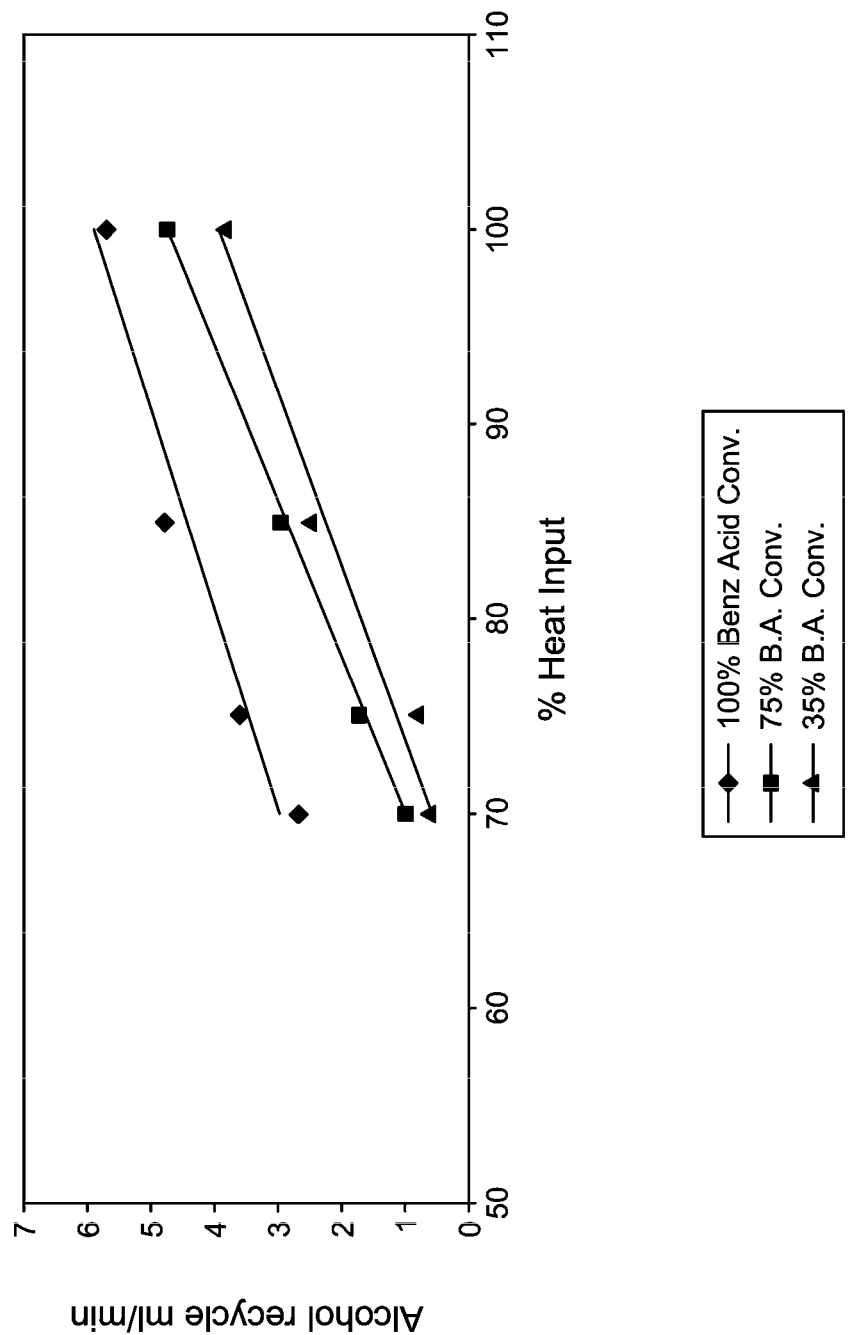
FIG. 6 shows the amount of reflux alcohol flowing back from the overhead in the second set of experiments.

The amount of reflux alcohol flowing back from the overhead condenser showed a linear correlation with the percentage of full heat input as shown in FIG. 6. Furthermore, the measured reflux rates are by extrapolation in line with those observed in commercial reactors by taking the ratio in $hr^{-1}$ between the reflux rate in mol/min and the final (100% acid conversion) ester batch size in mol followed by multiplying with 60.

In the experiments that contained benzoic acid, some esterification reaction was initiated even in the absence of Ti catalyst. In these experiments, foam developed due to formation of small droplets of water and although no flooding of the column was observed, the presence of foam reduced the alcohol reflux rate compared to the experiment that had no benzoic acid added (100% conversion case).

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the invention, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All priority documents are herein fully incorporated by reference for all jurisdictions in which such incorporation is permitted and to the extent such disclosure is consistent with the description of the present invention. Further, all documents and references cited herein, including testing procedures, publications, patents, journal articles, etc., are herein fully incorporated by reference for all jurisdictions in which such incorporation is permitted and to the extent such disclosure is consistent with the description of the present invention.

What is claimed is:

1. A process for production of $C_4$ to $C_{15}$ esters by an esterification reaction of an aromatic carboxylic acid with a $C_4$ to $C_{15}$ alcohol, the process comprising:
    (a) forming a reaction mixture of the aromatic carboxylic acid, a stoichiometric excess of the $C_4$ to $C_{15}$ alcohol at an initial temperature;
    (b) mixing the aromatic carboxylic acid and the alcohol at a temperature in the range from 100° C. to 160° C. and above the initial temperature of the reaction mixture;
    (c) adding an esterification catalyst to the reaction mixture and then heating the reaction mixture to a temperature in the range of from 180° C. to 200° C.; and
    (d) heating the reaction mixture containing the esterification catalyst to the esterification reaction temperature in the range of from 200° C. to 250° C., wherein the energy supply to the reaction mixture is reduced once the esterification reaction temperature is reached to reduce foaming.

2. The process according to claim 1, wherein the catalyst is a titanate.

3. The process according to claim 1, wherein the stoichiometric excess of the alcohol is from 20 to 30 mol %.

4. The process according to claim 1, wherein the alcohol has been purified by treatment with sodium borohydride.

5. The process according to claim 4, wherein the alcohol is a mixture of alcohols, at least one of the alcohols have been treated with sodium borohydride and another one of the alcohols have been hydrofined.

6. The process according to claim 1, wherein the aromatic carboxylic acid is benzoic acid and the alcohol is a $C_{10}$ alcohol.

7. The process according to claim 6, wherein the reduced energy supply is applied until at least 70% of the benzoic acid has been converted to a $C_{10}$ benzoate.

8. The process according to claim 1, wherein water is produced during the esterification reaction, and wherein after most of the reaction water has been removed, the energy supply is increased by increasing the energy supply to speed up completion of the esterification reaction.

9. The process according to claim 8, wherein the energy supply is increased after the esterification reaction is at least 70% complete.

10. The process according to claim 1, wherein the alcohol is a mixture of alcohols, and at least one of the alcohols have been treated with sodium borohydride; and wherein the energy supply is subsequently increased to enhance esterification reaction time.

11. The process according to claim 10, wherein the stoichiometric excess of the alcohol is from 20 to 30 mol %.

12. The process according to claim 10, wherein the aromatic carboxylic acid is benzoic acid and the alcohol is a $C_{10}$ alcohol.

13. The process according to claim 12, wherein the reduced energy supply is applied until at least 70% of the benzoic acid has been converted to a $C_{10}$ benzoate.

14. The process according to claim 10, wherein water is produced during the esterification reaction, and wherein after most of the reaction water has been removed, the energy supply is increased to speed up completion of the esterification reaction.

15. The process according to claim 14, wherein the energy supply is increased after the esterification reaction is at least 70% complete.

16. The process according to claim 1, wherein the energy supply to the reaction mixture is heat input.

17. The process of claim 16, wherein the heat input is reduced by 70%.

18. The process according to claim 1, wherein the energy supply to the reaction mixture is the intensity of the stirring.

19. The process according to claim 18, wherein the intensity of stirring is reduced by 50%.

20. The process according to claim 1, wherein the ratio of reflux flow rate in mol/min to the final batch size in mol times 60 is in the range of from 0.1 to 5 $h^{-1}$.

* * * * *